(12) United States Patent
Reed et al.

(10) Patent No.: US 6,239,169 B1
(45) Date of Patent: May 29, 2001

(54) NON-STEROIDAL POLYCYCLIC RING SULPHAMATE DERIVATIVES, THEIR PREPARATION AND THEIR USE AS OESTRONE SULPHATASE INHIBITORS

(75) Inventors: Michael J. Reed, London; Barry V. Potter, Bath, both of (GB)

(73) Assignee: Sterix Limited, Oxford (GB)

( * ) Notice: Subject to any disclaimer, the term of this patent is extended or adjusted under 35 U.S.C. 154(b) by 0 days.

(21) Appl. No.: 09/125,255

(22) PCT Filed: Feb. 17, 1997

(86) PCT No.: PCT/GB97/00444

§ 371 Date: Aug. 14, 1998

§ 102(e) Date: Aug. 14, 1998

(87) PCT Pub. No.: WO97/30041

PCT Pub. Date: Aug. 21, 1997

(30) Foreign Application Priority Data

Feb. 16, 1996 (GB) .................................................. 9603325

(51) Int. Cl.$^7$ ...................... A61K 31/352; A61K 31/366; C07D 311/78
(52) U.S. Cl. ............................................. 514/455; 549/280
(58) Field of Search ............................. 514/455; 549/280

(56) References Cited

U.S. PATENT DOCUMENTS

| 4,600,788 | 7/1986 | Creuzet et al. . |
| 4,618,622 | 10/1986 | Schlecker et al. . |
| 6,011,024 | 1/2000 | Reed et al. . |

FOREIGN PATENT DOCUMENTS

| 645975 | 2/1994 | (AU) . |
| 0 111 746 | 6/1984 | (EP) . |
| 0 403 185 | 12/1990 | (EP) . |
| 2 543 140 | 9/1984 | (FR) . |
| 93/05064 | 3/1993 | (WO) . |
| 97/32872 | 9/1997 | (WO) . |

OTHER PUBLICATIONS

Nelson et al. Experientia 39(7), 1983, pp. 740–742.*
Chemical Abstract, vol. 62(7), Abstract (a) p. 7670, 1965.*
Chemical Abstracts, J. Med. Chem., vol. 37, pp. 219–221 (1994).
Chemical Abstracts, J. Med. Chem., vol. 39, pp. 1349–1351 (1996).

* cited by examiner

Primary Examiner—Joseph McKane
Assistant Examiner—Taofiq A. Solola
(74) Attorney, Agent, or Firm—Frommer Lawrence & Haug LLP; Thomas J. Kowalski

(57) ABSTRACT

A non-steroidal compound suitable for use as an inhibitor of oestrone sulphatase. The compound has a polycyclic ring structure comprising two or more rings wherein at least two of the rings mimic the A and B rings of oestrone. The compound can have the general formula A wherein $R_1$–$R_6$ are independently selected from H, halo, hydroxy, sulphamate, alkyl and substituted variants or salts thereof; but wherein at least one of $R_1$–$R_6$ is a sulphamate group; and wherein X is any one of O, S, NH, a substituted N, $CH_2$ or a substituted C.

6 Claims, 4 Drawing Sheets

(A)

(B)

(C)

(D)

(E)

(F)

(G)

(H)

NON-STEROIDAL POLYCYCLIC RING SULPHAMATE DERIVATIVES, THEIR PREPARATION AND THEIR USE AS OESTRONE SULPHATASE INHIBITORS

RELATED APPLICATIONS

This application is the National Phase under 35 U.S.C. §371 of PCT/GB97/00444, filed Feb. 17, 1997, designating the U.S. and claiming priority from GB 9603325.3, filed Feb. 16, 1996.

The present invention relates to a compound.

In particular the present invention relates to a non-steroidal compound and to a pharmaceutical composition comprising the non-steroidal compound.

Evidence suggests that oestrogens are the major mitogens involved in promoting the growth of tumours in endocrine-dependent tissues, such as the breast and endometrium. Although plasma oestrogen concentrations are similar in women with or without breast cancer, breast tumour oestrone and oestradiol levels are significantly higher than in normal breast tissue or blood. In situ synthesis of oestrogen is thought to make an important contribution to the high levels of oestrogens in tumours and therefore specific inhibitors of oestrogen biosynthesis are of potential value for the treatment of endocrine-dependent tumours.

Over the past two decades, there has been considerable interest in the development of inhibitors of the aromatase pathway which converts the androgen precursor androstenedione to oestrone. However, there is now evidence that the oestrone sulphatase (E1-STS) pathway, i.e. the hydrolysis of oestrone sulphate to oestrone (E1S to E1), as opposed to the aromatase pathway, is the major source of oestrogen in breast tumours[1,2]. This theory is supported by a modest reduction of plasma oestrogen concentration in postmenopausal women with breast cancer treated by aromatase inhibitors, such as aminoglutethimide and 4-hydroxyandrostenedione[3,4] and also by the fact that plasma E1S concentration in these aromatase inhibitor-treated patients remains relatively high. The long half-life of E1S in blood (10–12 h) compared with the unconjugated oestrogens (20 min)[5] and high levels of steroid sulphatase activity in liver and, normal and malignant breast tissues, also lend support to this theory[6]. PCT/GB92/01587 teaches novel steroid sulphatase inhibitors and pharmaceutical compositions containing them for use in the treatment of oestrone dependent tumours, especially breast cancer. These steroid sulphatase inhibitors are sulphamate esters, such as N,N-dimethyl oestrone-3-sulphamate and, preferably, oestrone-3-sulphamate (otherwise known as "EMATE").

EMATE is a potent E1-STS inhibitor as it displays more than 99% inhibition of E1-STS activity in intact MCF-7 cells at 0.1 μM. EMATE also inhibits the E1-STS enzyme in a time- and concentration-dependent manner, indicating that it acts as an active site-directed inactivator[7,8]. Although EMATE was originally designed for the inhibition of E1-STS, it also inhibits dehydroepiandrosterone sulphatase (DHA-STS), which is an enzyme that is believed to have a pivotal role in regulating the biosynthesis of the oestrogenic steroid androstenediol[8,9]. Also, there is now evidence to suggest that androstenediol may be of even greater importance as a promotor of breast tumour growth[10]. EMATE is also active in vivo as almost complete inhibition of rat liver E1-STS (99%) and DHA-STS (99%) activities resulted when it is administered either orally or subcutaneously[11]. In addition, EMATE has been shown to have a memory enhancing effect in rats[14]. Studies in mice have suggested an association between DHA-STS activity and the regulation of part of the immune response. It is thought that this may also occur in humans[15,16]. The bridging O-atom of the sulphamate moiety in EMATE is important for inhibitory activity. Thus, when the 3-O-atom is replaced by other heteroatoms (FIG. 1) as in oestrone-3-N-sulphamate (4) and oestrone-3-S-sulphamate (5), these analogues are weaker non-time-dependent inactivators[12].

Although optimal potency for inhibition of E1-STS may have been attained in EMATE, it is possible that oestrone may be released during sulphatase inhibitions[8,12], and that EMATE and its oestradiol congener may possess oestrogenic activity[13].

The present invention therefore seeks to provide compounds suitable for the inhibition of E1-STS but which have no, or a minimal, oestrogenic effect.

According to a first aspect of the present invention there is provided a non-steroidal sulphamate compound suitable for use as an inhibitor of oestrone sulphatase, wherein the compound has a polycyclic ring structure comprising at least a first ring and a second ring; wherein the first ring and the second ring mimic the A and B rings of oestrone; and wherein the polycyclic ring structure is not tetrahydronaphthol.

Preferably either the first ring or the second ring comprises an α,β-unsaturated lactone group.

Preferably the first ring is a phenolic ring.

Preferably the compound has a bicyclic ring structure.

Preferably the compound has the general Formula (A) (see FIG. 8). In Formula (A) $R_1$–$R_6$ are independently selected from H, halo, hydroxy, sulphamate, alkyl and substituted variants or salts thereof; but wherein at least one of $R_1$–$R_6$ is a sulphamate group; and wherein X is any one of O, S, NH, a substituted N, $CH_2$, or a substituted C.

Preferably X is O.

Preferably, if the sulphamate group of the compound were to be replaced with a sulphate group to form a sulphate compound then that sulphate compound would be hydrolysable by an enzyme having steroid sulphatase (E.C. 3.1.6.2) activity.

In a highly preferred embodiment, the compound is not hydrolysable by an enzyme having steroid sulphatase (E.C. 3.1.6.2) activity.

According to a second aspect of the present invention there is provided a non-steroidal compound wherein the compound has the general Formula (B) (see FIG. 8). In Formula (B) $R_1$–$R_6$ are independently selected from H, halo, hydroxy, sulphamate, alkyl and substituted variants or salts thereof; but wherein at least one of $R_1$–$R_6$ is a sulphamate group.

According to a third aspect of the present invention there is provided the compound 4-methyl coumarin-7-0-sulphamate.

According to a fourth aspect of the present invention there is provided a non-steroidal compound according to the present invention for use as a pharmaceutical.

According to a fifth aspect of the present invention there is provided a non-steroidal compound according to the present invention for inhibiting oestrone sulphatase According to a sixth aspect of the present invention there is provided a pharmaceutical composition comprising a non-steroidal compound according to the present invention; and a pharmaceutically acceptable carrier, excipient or diluent.

According to a seventh aspect of the present invention there is provided the use of a non-steroidal compound according to the present invention in the manufacture of a pharmaceutical for inhibiting oestrone sulphatase.

According to an eighth aspect of the present invention there is provided a process for preparing a compound according to the present invention, the process comprising sulphating a coumarin.

According to a ninth aspect of the present invention there is provided a process for preparing a compound according to the present invention, the process comprising sulphamaylating a coumarin.

The alkyl group(s) in Formula (A) or Formula (B) can be any suitable linear or branched alkyl group which may be saturated or unsaturated and/or substituted or non-substituted. The alkyl group may even be a cyclic alkyl group. For example, at least two of $R_{1-6}$ are linked to form a further cyclic component.

Preferably $R_1$–$R_5$ are independently selected from H, alkyl and haloalkyl; preferably wherein $R_1$–$R_5$ are independently selected from H, C1–6 alkyl and C1–6 haloalkyl.

Preferably $R_1$–$R_5$ are independently selected from H, C1–3 alkyl and C1–3 haloalkyl.

Preferably $R_1$–$R_5$ are independently selected from H, methyl and halomethyl. Preferably $R_6$ is $OSO_2NH_2$.

Preferably the compound is any one of the compounds shown as Compounds 12–16 in FIG. 2.

Preferably the compound is 4-methyl coumarin-7-O-sulphamate.

In Formula (A) or Formula (B), two or more of $R_1$–$R_6$ may be linked together to form an additional cyclic structure. A typical example of such a compound has the general Formula (C) (see FIG. 8), wherein any one of $R_3$–$R_6$ is a sulphamate group, and wherein n is an integer. Typically, $R_6$ is a sulphamate group. A typical sulphamate group is —OS(O)(O)—$NH_2$. Preferably n is an integer of from 3 to 10, preferably from 3 to 7. Optionally, the group (CH2)n of Formula (C) can be a substituted alkyl chain.

Typical compounds falling within the general Formula (C) are shown as compound (D) (where n=3), compound (E) (where n=4), compound (F) (where n=5), compound (G) (where n=6), compound (H) (where n=7). For these compounds, $R_6$ is a sulphamate group of the formula —OS(O)(O)—$NH_2$ and each of $R_3$–$R_5$ is H.

The term "sulphamate" as used herein includes an ester of sulphamic acid, or an ester of an N-substituted derivative of sulphamic acid, or a salt thereof. Thus, the term includes-functional groups of the formula:—O—S(O)(O)—N($R_7$)($R_8$) where $R_7$ and $R_8$ are independently selected from H, halo, linear or branched alkyl which may be saturated or unsaturated and/or substituted or non-substituted, aryl, or any other suitable group, Preferably, at least one of $R_7$ and $R_8$ is H. In a preferred embodiment, each of $R_7$ and $R_8$ is H.

The term "mimic" as used herein is used in its normal sense—namely having a different structure but having a similar functional effect.

A key advantage of the non-steroidal compound of the present invention is that it is potent in vivo and that it has less oestrogenic activity and can therefore be deemed to be a "non-oestrogenic compound". The term "non-oestrogenic compound" as used herein means a compound exhibiting no or substantially no oestrogenic activity.

The present invention therefore provides non-steroidal compounds which have a reduced oestrogenic activity. In this regard, the non-steroidal compounds of the present invention act as E1-STS inhibitors.

Another advantage is that the compounds may not be capable of being metabolised to compounds which display or induce hormonal activity.

The compounds of the present invention are also advantageous in that they are orally active.

The compounds of the present invention are further advantageous in that they may have an irreversible effect.

The compounds of the present invention are further advantageous in that they may also inhibit DHA-STS.

Thus, in a preferred embodiment, the non-steroidal compounds are useful for the treatment of breast cancer. In addition, the non-steroidal compounds are useful for the treatment of non-malignant conditions, such as the prevention of auto-immune diseases, particularly when pharmaceuticals may need to be administered from an early age.

A particularly preferred non-steroidal compound according to the present invention is 4-methyl coumarin-7-O-sulphamate. This compound is particularly advantageous in that it acts as a time- and a concentration-dependent inhibitor in a similar manner to EMATE. Another key advantage of this non-steroidal compound is that it is an orally active irreversible compound. In addition, it is not metabolised to compounds with hormonal activity.

A highly preferred embodiment of the present invention therefore relates to a pharmaceutical composition comprising 4-methyl coumarin-7-O-sulphamate and a pharmaceutically acceptable carrier, excipient or diluent.

The present invention therefore relates to non-steroidal compounds which are suitable for use as sulphatase inhibitors.

In addition to being potent in vivo sulphatase inhibitors, the compounds of the present invention have reduced, or even minimal or no, oestrogenic activity.

Studies have shown that the sulphamates of the present invention inhibit enzyme E1-ETS in intact MCF-7 cells in a dose dependent manner with similar potencies to EMATE.

Of the preferred coumarin sulphamates, 4-methylcoumarin-7-O-sulphamate together with coumarin-7-O-sulphamate appear most active in vitro. In this regard, 4-methylcoumarin-7-O-sulphamate inhibited E1-STS by 93.3% at 10 $\mu$M with an IC$_{50}$ of 380 nM in intact MCF-7 breast cancer cells. This inactivation was shown to be time- and concentration-dependent inhibitor in a similar way to EMATE. 4-methylcoumarin-7-O-sulphamate also inhibited placental microsomal dehydro-epiandrosterone sulphatase by 93.6% at 10 $\mu$M. This compound also shows a reduced oestrogenic activity as was seen by the lack of significant increase in the uterine weight in treated ovariectomised rats.

The compound also has a potent oral activity.

The non-steroidal compounds of the present invention, in particular the preferred coumarin sulphamates, represent important compounds for the optimisation of non-steroidal sulphatase inhibition. The compounds are also believed to have therapeutic uses other than for the treatment of endocrine-dependent cancers, such as the treatment of autoimmune diseases.

BRIEF DESCRIPTION OF THE DRAWINGS

The present invention will now be described only by way of example with reference to the accompanying drawings in which.

EXAMPLES

The compounds of the present invention may be- prepared by a process that comprises a Packman synthesis step. Packman synthesis is known in the art.

Sulphamoylation of coumarins

Figure 4:
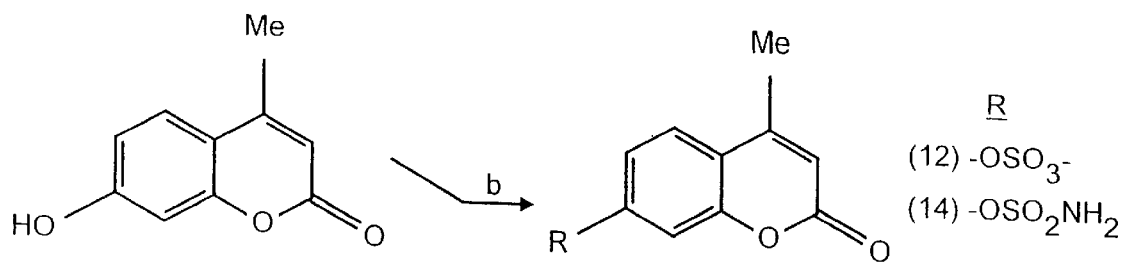
FIG. 4 shows the sulphamoylation of 7-hydroxy4-methylcoumarin; NaH/DMF, $H_2NSO_2Cl$ in toluene (Route b)

The general procedure for the sulphamoylation of coumarins was as follows. A solution of an appropriate coumarin in anhydrous DMF (ca. 40 ml per g of coumarin) was treated with sodium hydride [60% dispersion; 1equiv] at 0° C. under an atmosphere of $N_2$. After evolution of hydrogen had ceased, sulphamoyl chloride in toluene [ca. 0.68 M, 1.5 equiv] was added and the reaction mixture was poured into water after warming to room temperature overnight and then the crude product was then quenched. The organic fraction in ethyl acetate (150 ml) was washed exhaustively with brine, dried ($MgSO_4$), filtered and evaporated. The crude product obtained was purified by flash chromatography followed by recrystallisation to give the corresponding sulphamate. All new compounds were fully characterised by spectroscopic and combustion analysis. The synthesis of 4 methylcoumarin-7-O-sulphamate (14) is shown in FIG. 4.

Figure 1:
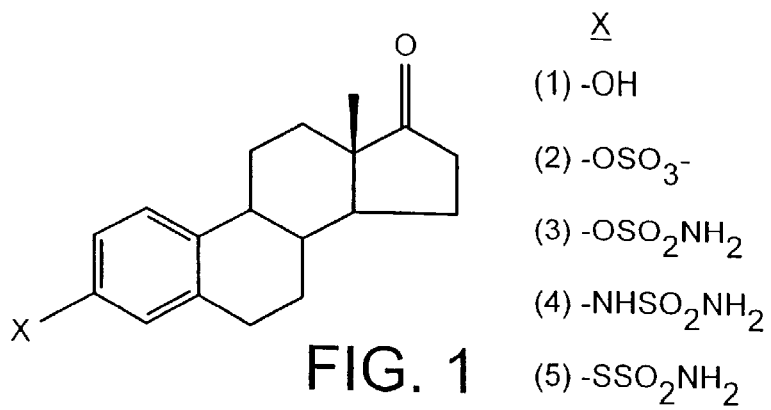
FIG. 1 shows the known structures of oestrone (1), oestrone sulphate (2), EMATE (3) and steroid sulphamates (4–5)
Figure 2:
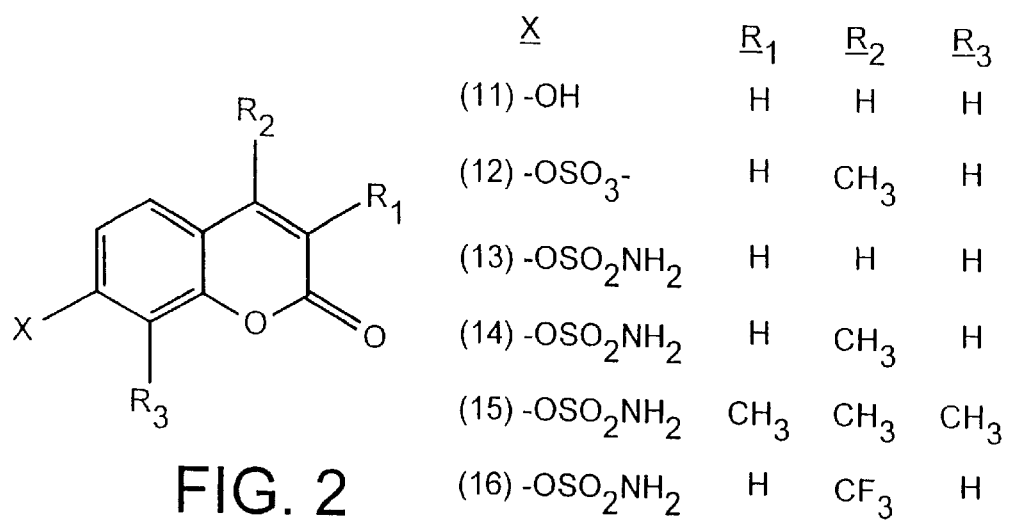
FIG. 2 shows the structures of 7-hydroxycoumarna (11), 7-(sulphoxy)4-methylcoumarin (12) and coumarin sulphamates (13–16)

Following this general procedure, compounds 13–16 (as shown in FIG. 2) - i.e. coumarin-7-O-sulphamate (13), 4-methylcoumarin-7-O-sulphamate (14), 3,4,8-trimethylcoumarin-7-O-sulphamate (15) and 4-(trifluoromethylcoumarin)-7-O-sulphamate (16) - were prepared. More details on the synthesis of these compounds now follow.

The synthesis of compound 12 (as shown in FIG. 2) is also discussed below.

Preparation of Coumarin-7-O-sulphamate (13)

Following the above-mentioned general procedure, 7-Hydroxycoumarin (500 mg, 3.082 mmol) gave a crude product (605 mg) which was fractionated on silica (200 g) by gradient elution with chloroform/acetone (8:1, 500 ml; 4:1, 1000 ml and then 2:1, 500 ml). Upon evaporation, the second fraction gave a creamy yellow residue (389 mg, 52.3%) which was recrystallised in ethyl acetate/hexane (1:1) to give (13) as dull white crystals (239 mg).

Analytical data were as follows:

M.p. 170.0–171.5° C.; $R_f$s=0.48 (ether), 0.67 (ethyl acetate), 0.19 (chloroform/acetone, 4:1); νmax (KBr) 3360, 3210, 3060, 1720, 1615, 1370, 1125 cm$^{-1}$; $δ_H$(DMSO-$d_6$/CDCl$_3$, ca. 1:25) 6.415 (1H, d, $J_{C-4-H, C-3-H}$=9.7 Hz, C-3-H), 7.285 (1H, dd, $J_{C-8-H, C-6-H}$=2.3 Hz and $J_{C-5-H, C-6-H}$=8.5 Hz, C-6-H), 7.379 (1H, d, $J_{C-6-H, C-8-H}$=2.2 Hz, C-8-H), 7.508 (2H, br S, $D_2O$ exchanged, -$NH_2$), 7.543 (1H, d, $J_{C-6-H, C-5-H}$=8.4 Hz, C-5-H) and 7.760 (1H, d, $J_{C-3-H, C-4-H}$=9.7 Hz, C-4-H). MS:m/z (E.I., rel. intensity) 241.0(10), 162.0(97), 134.0(100), 105.0(23). Acc. MS: m/z 241.0068, $C_9H_7NO_5S$ requires 241.0045. Found:C, 44.8; H, 2.89; N, 5.82. $C_9H_7NO_5S$ requires C, 44.81; H, 2.92; N, 5.81%.

Preparation of 4-Methylcoumarin-7-O-sulphamate (14)

Following the above-mentioned general procedure, 7-Hydroxy4-methylcoumarin(500 mg, 2.753 mmol) gave a crude product (633 mg) which was fractionated on silica (200 g) by gradient elution with chloroform/acetone (8:1, 500 ml; 4:1, 1000 ml, 2:1, 500 ml and then 1:1, 500 ml). Upon evaporation, the second fraction gave a creamy yellow residue (425 mg, 60.5%) which was recrystallised in acetone/chloroform (3:5) to give (14) as colorless rhombic crystals (281 mg).

Analytical data were as follows:

M.p. 165–167° C.; $R_f$s=0.48 (ether), 0.29 (ether/hexane 8:1), 0.26 (chloroform/acetone, 4:1); νmax (KBr) 3320, 3180, 3080, 1700, 1620, 1560, 1380, 1125 cm$^{-1}$; $δ_H$(acetone-$d_6$) 2.507 (3H, s, —$CH_3$), 6.339 (1H, s, C-3-H), 7.299 (2H, m, C-6-H and C-8-H), 7.390 (2H, br s, $D_2O$ exchanged, —$NH_2$) and 7.850 (1H, d, $J_{C-6-H, C-5-H}$=9 Hz, C-5-H). MS:m/z (+ve ion FAB in m-NBA, rel. intensity) 542.2(15), 511.1[45, (2M+H)$^+$], 461.2(20), 409.1[60, (M+H+NBA)$^+$], 393.3[60, (M+H+NBA-16)$^+$], 329.2[10, (M+H+NBA-80)$^+$], 256.1 [100, (M+H)$^+$], MS:m/z (-ve ion FAB in m-NBA, rel. intensity) 421.0(20), 407.1[15, (M–H+NBA)$^-$], 335.1(14), 254[100, (M–H)$^-$], 175.1[32, (M–H–79)$^-$], 121.0(17). Found:C, 47.2H, 3.56; N, 5.51. $C_{10}H_9NO_5S$ requires C, 47.06; H, 3.55; N, 5.49%.

Preparation of 3,4.8-Trimethylcoumarin-7-O-sulphamate (15)

Following the above-mentioned general procedure, 7-Hydroxy-3,4,8-trimethylcoumarin (1.0 g, 4.896 mmol) gave a crude product (1.33 g) which upon recrystallisation in hot ethyl acetate yielded 238 mg of starting coumarin. The mother liquor was evaporated and the white residue obtained (1.13 g) was fractionated on silica (200 g) with ether. The second fraction was collected, evaporated and the residue obtained (519 mg, 37.4%) was recrystallised in acetone/hexane (1:2) to give (15) as pale yellow crystals (312 mg).

Analytical data were as follows:

M.p. 197–202° C.; $R_f$s=0.50 (ether), 0.69 (ethyl acetate); νmax (KBr) 3310, 3040, 1680, 1600 cm$^{-1}$; $δ_H$ (acetone-$d_6$) 2.176, 2.383 and 2.458 (9H, three s, 3×$CH_3$), 7.374 (1H, d, $J_{C-5-H, C-6-H}$=8.8 Hz, C-6-H), 7.390 (2H, br s, $D_2O$ exchanged, —$NH_2$) and 7.682 (1H, d, $J_{C-6-H, C-5-H}$=8.8 Hz, C-5-H). MS:m/z (E.I., rel. intensity) 283.1(10), 204.1(45), 176.1(40), 161.1(22), 69.1(56), 57.1(40), 43.1(100). Acc. MS:m/z 283.0497, $C_{12}H_{13}NO_5S$ requires 283.0514. Found:C, 50.86; H, 4.63; N, 4.97. $C_{12}H_{13}NO_5S$ requires C, 50.88; H, 4.63; N, 4.94%.

Preparation of 4-(Trifluoromethyl)coumarin-7-O-sulphamate (16)

Following the above-mentioned general procedure, 7-Hydroxy4-(trifluoromethyl)-coumarin (0.90 g, 3.911 mmol) gave a crude product (1.20 g) which was fractionated on silica (200 g) with ether/chloroform (1:4). The residue (392 mg) from the third fraction was further purified by fractionating on silica (100 g) with ether. The first fraction then collected gave a residue (295 mg, 24.4%) which upon recrystallised in ethyl acetate/hexane (1:3) gave (16) as white needle-shaped crystals (160 mg).

Analytical data were as follows:

M.p. 165–168° C.; $R_f$s=0.67 (ether), 0.24 (ether/chloroform, 1:4); vmax (KBr) 3360, 3240, 3100, 1720, 1620, 1380, 1160 cm$^{-1}$; $\delta_H$(acetone-d$_6$) 6.995 (1H, s, C-3-H), 7.461 (1H, dd, $J_{C-8-H, C-6-H}$=2.8 Hz and $J_{C-5-H, C-6-H}$=8.1 Hz, C-6-H), 7.478 (1H, s, C-8-H), 7.53 (2H, br s, D$_2$O exchanged, —NH$_2$) and 7.89 (1H, m, C-5-H). $^1$H-NMR spectrum of (16) in DMSO-d$_6$/CDCl$_3$(ca. 1:15) showed partial decompostion to the starting coumarin. MS:m/z (E.I., rel. intensity) 309.0(2.6), 230.0(77), 202.0(100), 183.5(5), 173.0(10), 69.0(33). Acc. MS:m/z 308.9874, C$_{10}$H$_6$F$_3$NO$_5$S requires 308.9919. Found:C, 38.8; H, 1.85; N, 4.53. C$_{10}$H$_6$F$_3$NO$_5$S requires C, 38.84; H, 1.96; N, 4.53%.

Preparation of 7-(Sulphoxy)-4-Methylcoumarin, sodium salt (12)

Figure 3:
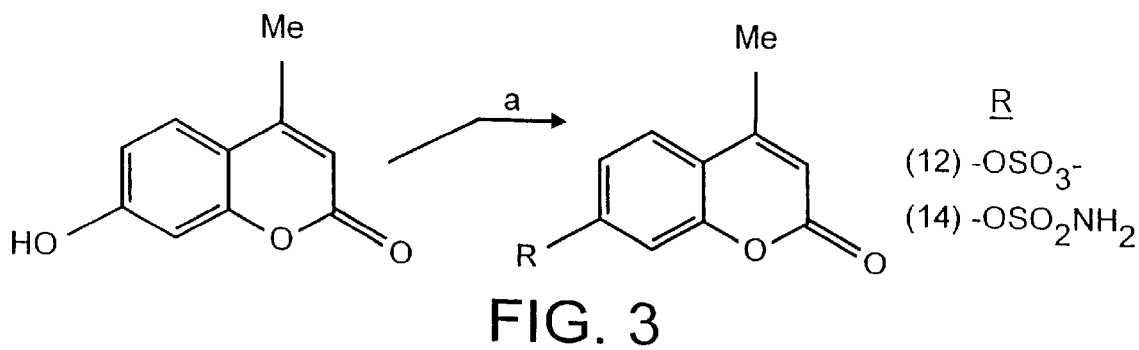
FIG. 3 shows the sulphation of 7-hydroxy4-methylcoumarin; pyridine/$SO_3$-pyridine complex, NaOR in MeOH (Route a)

To a solution of 7-hydroxy-4-methylcoumarin (1.0 g, 5.676 mmol) in dried pyridine (20 ml) under an atmosphere of N$_2$ [FIG. 3] was added sulphur trioxide-pyridine complex (1.8 g, 11.35 mmol, 2 equiv.) and the reaction mixture was stirred overnight. After removal of pyridine, methanol (20 ml) was added to the creamy syrup obtained and the resulting light yellow solution was basified (pH~8) by dropwise addition of sodium hydroxide in methanol (1 M, ca. 18 ml). The bright yellow suspension formed was filtered and the precipitated washed with more methanol. The filtrate was then concentrated to 30–40 ml and ether (total 120 ml) was added in portions until precipitation completed. The light beige precipitate was collected (711 mg) and 582 mg of which was recrystallised in methanol/ether (1:1) to give (12) as light creamy yellow crystals (335 mg).

Analytical data were as follows:

M.p. 172–175° C. (dec.); $R_f$s=0.51 (methanol/ethyl acetate, 1:3), 0.67 (methanol/ether, 1:3); vmax (KBr) 3500 (br), 3080, 1680, 1610, 1560, 1300, 1260, 1050 cm$^{-1}$; $\delta^H$ (DMSO-d$_6$) 2.407 (3H, s, —CH$_3$), 6.269 (1H, s, C-3-H), 7.20 (2H, m, C-6-H and C-8-H), and 7.695 (1H, d, $J_{C-6-H, C-5-H}$=8.8 Hz, C-5-H). MS:m/z (+ve ion FAB in m-NBA, rel. intensity) 176(100, NBA+N$^+$). MS:m/z (-ve ion FAB in m-NBA, rel. intensity) 175.1 (14, M−Na$^+$—SO$_3$), 255.0 (100, M−Na$^+$), 408.0 (8, M−Na$^+$+NBA), 431.0 (15, M+153), 444.0(20), 533.0(15). 230.0(77), 202.0(100), 183.5 (5), 173.0(10), 69.0(33). Acc. MS:mlz (-ve ion FAB in glycerol, rel. intensity) 254.9982(25), C$_{10}$H$_7$O$_6$S requires 254.9963. Found:C, 40.3; H, 2.92. C$_{10}$H$_7$O$_6$NaS H$_2$O requires C, 40.55; H, 3.06%. HPLC [Spherisorb ODS5, 25×4.6 mm; Mobile phase:MeOH/H$_2$O (70:30), Flow rate:1 ml/min; $\lambda_{max}$:316 nm]:t$_R$=1.5 min, c.f. 7-hydroxy-4-methylcoumarin, 3.6 min.

Other data were as follows:

Compound 12 is stable in bases such as sodium hydroxide in methanol but not in acidic conditions. In addition, incomplete basification of the reaction mixture with sodium hydroxide in methanol (<3 equivalents) leads to decomposition of (12). Two equivalents of sodium hydroxide are required for consuming excess sulphur trioxide-pyridine complex to yield the neutral sodium sulphate. Insufficient amount of sodium hydroxide will therefore lead to the formation of sodium hydrogen sulphate which is acidic. Compound 12 appears labile to high temperature as one experiment has shown complete decomposition to 7-hydroxy-4-methylcoumarin after heating (12) as solid at 90° C. for 4 h.

In vitro tests

The above-mentioned coumarin sulphamates were tested for their ability to inhibit E1-STS activity using intact MCF-7 breast cancer cells or placental microsomes (100, 000 g fraction) essentially as previously described.

To examine whether compound (12) could act as a substrate for E1-STS, 100 $\mu$g of the compound was incubated for 1 hour with placental microsomes in the absence or presence of EMATE (10 $\mu$M). The unconjugated coumarin formed at the end of the incubation was extracted with diethyl ether. After evaporation of solvent, the residue was examined by TLC using ethyl acetate/methanol (80:20) as eluent, in which the coumarin sulphate (12) and 7-hydroxy4-methylcoumarin had R$_f$ values of 0.79 and 0.95 respectively. Only unconjugated 7-hydroxy-4-methylcoumarin was detected after incubation of compound (12) with placental microsomes. The inclusion of EMATE in the reaction mixture reduced the hydrolysis of compound (12) by E1-STS, indicating that the coumarin sulphate is indeed a substrate for the sulphatase.

Figure 5:
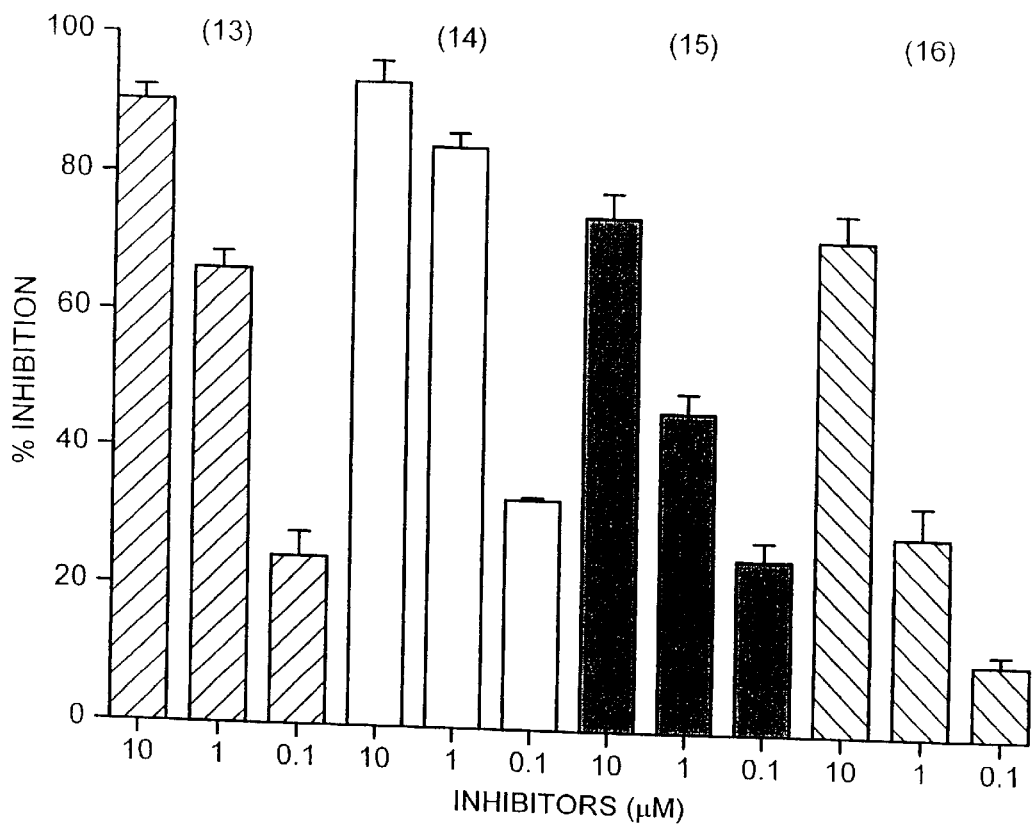
FIG. 5 shows the dose-dependent inhibition of oestrone sulphatase in intact MCF-7 breast cancer cells by coumarin-7-O-sulphamate (13), 4-methylcoumarin-7-O-sulphamate (14), 3,4,8-trimethyl-coumarin-7-O-sulphamate (15) and 4-(trifluoromethyl)coumarin-7-O-sulphamate (16)

The dose-dependent inhibition of oestrone sulphatase in intact MCF-7 breast cancer cells by coumarin-7-O-sulphamate (13), 4-methylcoumarin-7-O-sulphamate (14), 3,4,8-trimethyl-coumarin-7-O-sulphamate (15) and 4-(trifluoromethyl)coumarin-7-O-sulphamate (16) can be seen from FIG. 5. Assays were performed essentially as previously described.(7, 8) Monolayers of intact MCF-7 cells in 25 cm$^3$ flasks were incubated for 20 h at 37° C. with [$^3$H]oestrone sulphate (2 nM) and coumarin sulphamates at 0.1–10 $\mu$M. Oestrone sulphatase activity was determined by measuring the total amount of $^3$H-labeled oestrone and oestradiol formed. Sulphatase activity in untreated cells was 100–200 fmol/20 h/10$^6$ cells. Each point represents the mean ±s.d. of triplicate measurements.

The free parent coumarins of all coumarin sulphamates prepared showed little or no E1-STS inhibitory activity when tested up to 10 $\mu$M. However, in contrast, all four coumarin sulphamates (compounds 13–16) inhibited oestrone sulphatase inhibitory activity in a dose-dependent manner (FIG. 5) and the inhibition at 10 $\mu$M ranged from 71.5% for compound 16 to 93.3% for compound 14. The IC$_{50}$ for inhibition of E1-STS by compound 14, the most effective inhibitor, measured using intact MCF-7 cells was 380 nM.

Figure 6:
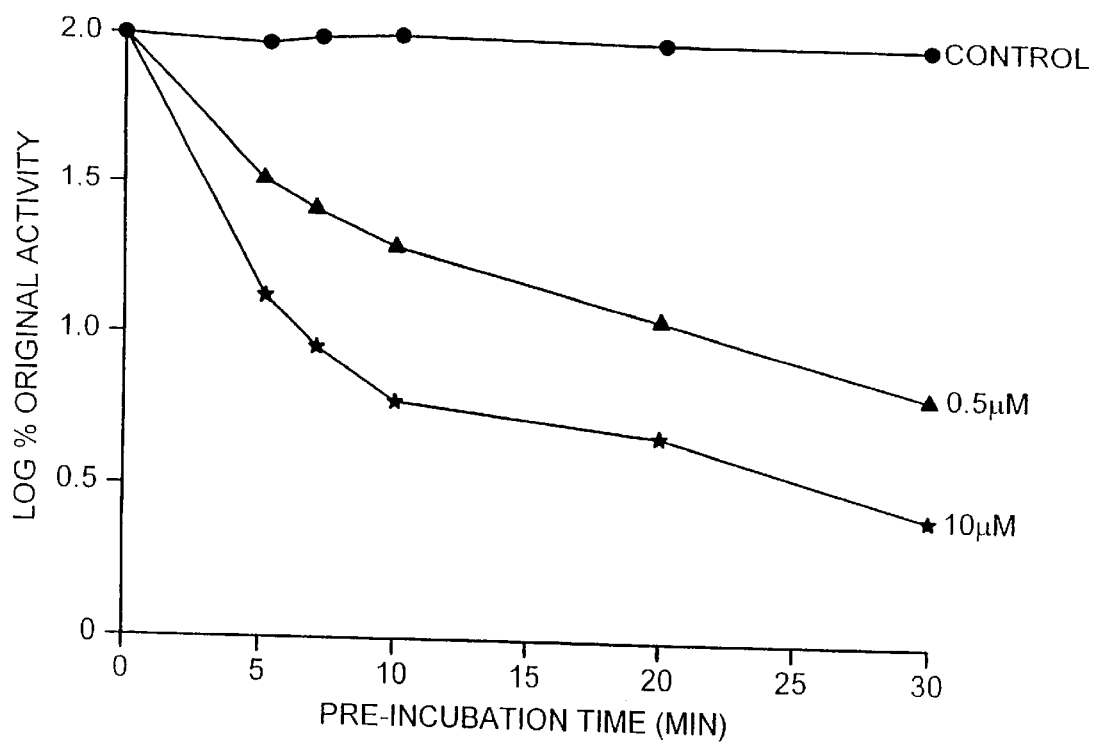
FIG. 6 shows the time-dependent and the concentration-dependent inactivation of oestrone sulphatase by 4-methyl-coumarin-7-O-sulphamate (14)

The time- and concentration-dependent inactivation of oestrone sulphatase by 4-methyl-coumarin-7-O-sulphamate (14) can be seen from FIG. 6. Placental microsomes (200 $\mu$g) were preincubated with (14) (control,●; 0.5 $\mu$M, Δ and 10 $\mu$M, *) for 0–30 min at 37° C. followed by incubation with dextran-charcoal for 10 min at 4° C. Dextran-charcoal was sedimented by centrifugation and portions of the supernatants were then incubated with [$^3$H]oestrone sulphate (20 $\mu$M) for 1 h at 37° C. to assess remaining sulphatase activity. Duplicate experiments were run at each concentration, but assays for residual activity were taken at different times in each experiment.

As with EMATE, compound 14 inhibited E1-STS activity in a time- and concentration-dependent manner in a biphasic fashion (FIG. 6), indicating a similar mechanism of action (potential chemical modification of two active site residues). At 10 $\mu$M, compound 14 reduced the original E1-STS activity by 95% after preincubating the enzyme with the inhibitor for 20 min.

Additional experiments revealed that compound 14 inhibited placental microsomal DHA-STS activity by 93.6% at the same concentration.

In Vivo Tests

In order to examine if compound 14 possessed oestrogenic activity and also to test its ability to inhibit E1-STS in vivo, it was administered to rats (1 mg/kg subcutaneously, in propylene glycol for 5 days) 14 days after ovariectomy had been performed.

Administration of compound 14 did not result in any significant increase in the uterine weight in these rats (data not shown), showing that compound 14 showed reduced oestrogenic agonist properties. The E1-STS activity in the uteri obtained from these animals was inhibited by 89.4% compared with the activity in untreated animals.

Preliminary data also demonstrate potent oral activity in rats for compound 14, similar to that observed for EMATE.

In addition to these in vivo results, another series of rats (each weighing approximately 200g) received 4-methyl coumarin-7-0-sulphamate (compound 14) orally in propylene glycol either as a single dose (SD) or daily for seven days (Multiple Dose, MD).

Inhibition of sulphatase activity was assessed in white blood cells (wbcs) that were collected after a SD or MD. Sulphatase activity was assayed using labelled oestrone sulphate as the substrate and measuring the release of oestrone.

Figure 7:
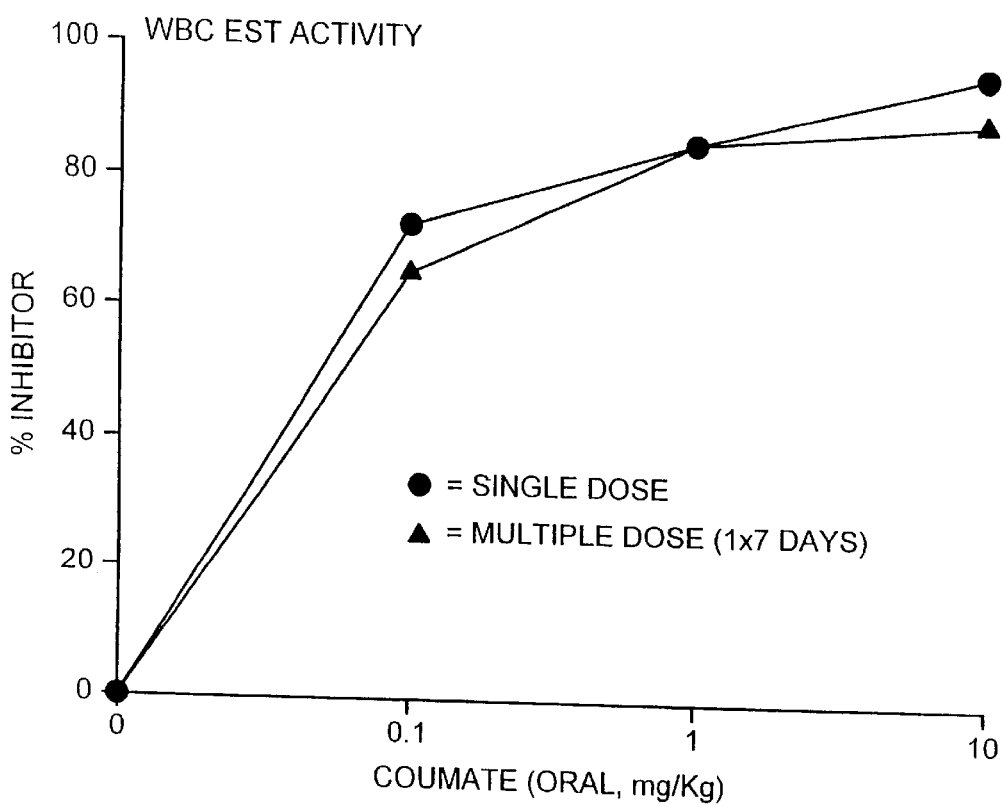
FIG. 7 is a graph showing the percent inhibition vs. Coumate (oral, mg/kg)
Figure 8:
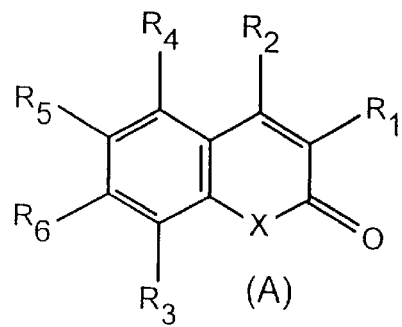
FIG. 8 presents Formulae (A), (B) (C), (D), (E), (F), (G) and (H).
Figure 8:
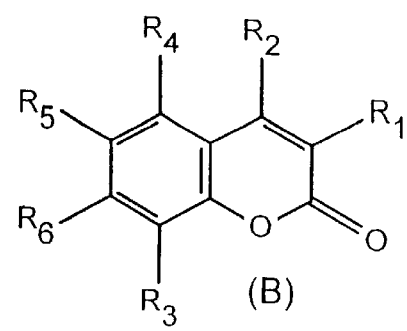
Figure 8:
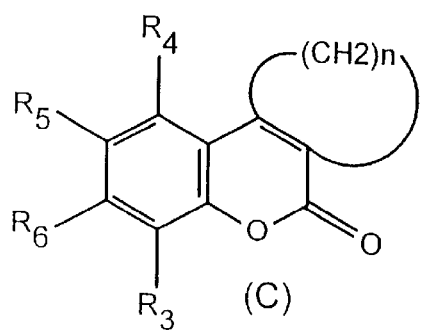
Figure 8:
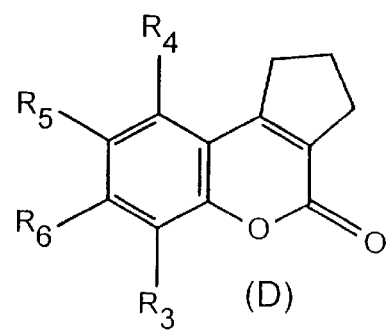
Figure 8:
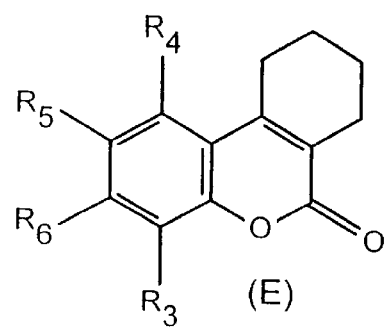
Figure 8:
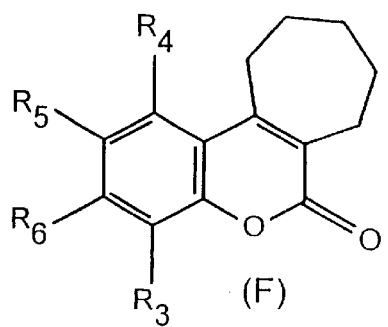
Figure 8:
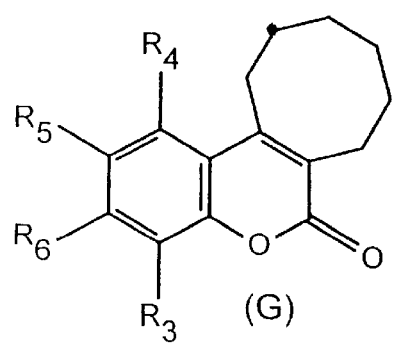
Figure 8:
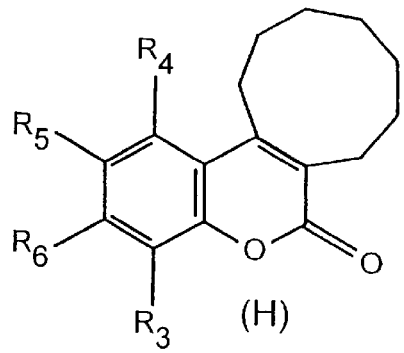

The results are shown in FIG. 7 and in the Table below:

| Dose | % Inhibition | |
| --- | --- | --- |
| mg/kg | SD | MD |
| 0.1 | 72 | 65 |
| 1.0 | 85 | 85 |
| 10.0 | 96 | 89 |

Similar results were found with liver cells.

Compound 14 therefore demonstrates potent oral activity.

Other modifications of the present invention will be apparent to those skilled in the art.

REFERENCES (1) Santner, S. J.; Feil, P. D.; Santen, R. J. In situ oestrogen production via the oestrone sulphatase pathway in breast tumors:relative importance vs. the aromatase pathway. *J. Clin. Endocrinol. Metab.* 1984, 59, 29–33.

(2) Yamamoto, T.; Kitawaki, J.; Urabe, M.; Honjo, H.; Tamura, T.; Noguchi, T.; Okada, H.; Sasaki, H.; Tada, A.; Terashima, Y.; Nakamura, I.; Yoshihama, M. Oestrogen productivity of endometrium and endometrial cancer tissue—influence of aromatase on proliferation of endometrial cancer cells. *J. Steroid Biochem. Mol. Biol.* 1993, 44, 463–468.

(3) Santen, R. J.; Santner, S. J.; Davis, B.; Veldhuis, J.; Samojilik, E.; Ruby, E. Aminogluthethimide inhibits extraglandular oestrogen production in post-menopausal women with breast carcinoma. *J. Clin. Endocrinol. Metab.* 1978, 47, 1257–1265.

(4) Reed, M. J.; Lai, L. C.; Owen, A. M.; Singh, A.; Coldham, N. G.; Purohit, A.; Ghilchik, M. W.; Shaikh, N. A.; James, V. H. T. Effect of treatment with 4-hydroxy-androstenedione on the peripheral conversion of androstenedione to oestrone and in vitro tumour aromatase activity in postmenopausal women with breast cancer. *Cancer Res.* 1990, 50, 193–196.

(5) Ruder, H. J.; Loriaux, D. L.; Lipsett, M. B. Oestrone sulphate:production rate and metabolism in man. *J. Clin. Invest.* 1972, 51, 1020–1023.

(6) James, V. H. T.; McNeill, J. M.; Lai, L. C.; Newton, C. J.; Ghilchik, M. W.; Reed, M. J. Aromatase activity in normal breast and breast tumor tissues:in vivo and in vitro studies. *Steroids* 1987, 50, 269–279.

(7) Howarth, N. M.; Purohit, A.; Reed, M. J.; Potter, B. V. L. Oestrone sulphamates:potent inhibitors of oestrone sulphatase with therapeutic potential. *J. Med. Chem.* 1994, 37, 219–221.

(8) Purohit, A.; Williams, G. J.; Howarth, N. M.; Potter, B. V. L.; Reed, M. J. Inactivation of steroid sulphatase by an active site-directed inhibitor, oestrone-3-O-sulphamate. *Biochemistry* 1995, 34, 11508–11514.

(9) Purohit, A.; Dauvois, S.; Parker, M. G.; Potter, B. V. L.; Williams, G. J.; Reed, M. 3. The hydrolysis of oestrone sulphate and dehydroepiandrosterone sulphate by human steroid sulphatase expressed in transfected COS-1 cells. *J. Steroid Biochem. Mol. Biol.* 1994, 50, 101–104.

(10) Dauvois, S.; Labrie, F. Androstenedione and androst-5-ene-3$\beta$,17$\beta$B-diol stimulate DMBA-induced rat mammary tumours - role of aromatase. *Breast Cancer Res. Treat.* 1989, 13, 61–69.

(11) Purohit, A.; Williams, G. J.; Roberts, C. J.; Potter, B. V. L.; Reed, M. J. In vivo inhibition of oestrone sulphatase and dehydroepiandrosterone sulphatase by oestrone-3-O-sulphamate. *Int. J. Cancer* 1995, 63, 106–111.

(12) Woo, L. W. L.; Lightowler, M.; Purohit, A.; Reed, M. J.; Potter, B. V. L. Heteroatom-substituted analogues of the active-site directed inhibitor oestra-1,3,5(10)-trien-17-one-3-sulphamate inhibit oestrone sulphatase by a different mechanism. *J. Steroid Biochem. Mol. Biol.* 1996 (in press).

(13) Elger, W.; Schwarz, S.; Hedden, A.; Reddersen, G.; Schneider, B. Sulphamates of various oestrogens-prodrugs with increased systemic and reduced hepatic oestrogenicity at oral application. *J. Steroid Biochem. Mol. Biol.* 1995, 55, 395–403.

(14) Li, P. K; Rhodes, M. E.; Jagannathan, S; Johnson, D. A. Memory enhancement mediated by the steroid sulphatase inhibitor oestrone 3-O-sulphamate. *J. Endocrinol.* 1995, 144, Abstr. P155.

(15) Daynes, R. A.; Araneo, B. A.; Dowell, T. A.; Huang, K.; Dudley, D. Regulation of murine lymphokine production in vivo. 3. The lymphoid tissue micro-environment exerts regulatory influences over T-helper cell function. *J. Exp. Med.* 1990, 171, 979–996.

(16) Rook, G. A. W.; Hernandez-Pando, R.; Lightman, S. Hormones, peripherally activated prohormones and regulation of the TH1/TH2 balance. *Immunol. Today* 1994, 15, 301–303.

What is claimed is:

1. A compound selected from the group consisting of compounds D, E, F, G and H, wherein $R_3$ to $R_6$ are independently selected from H, halo, hydroxy, sulphamate, alkyl, and substituted aryl, wherein at least one of $R_3$ to $R_6$ is a sulphamate group; or salts thereof

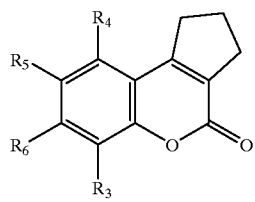
(D)

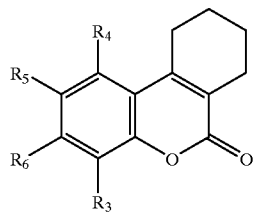
(E)

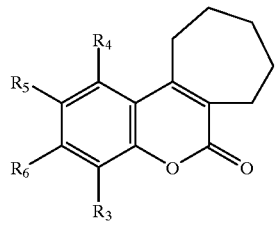
(F)

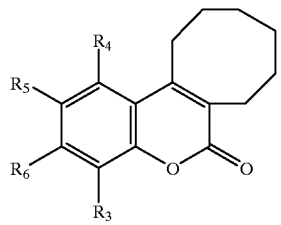
(G)

and

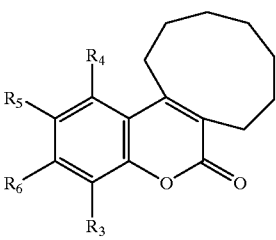
(H)

2. The compound of claim 1 which is compound F.

3. A pharmaceutical composition comprising a non-steroidal compound according to any one of claims 1 or 2 and a pharmaceutically acceptable carrier, excipient or diluent.

4. A composition for inhibiting oestrone sulphatase comprising a non-steroidal compound according to any one of claims 1 or 2 and a pharmaceutically acceptable carrier, excipient or diluent.

5. A method for preparing a pharmaceutical composition comprising admixing a non-steroidal compound according to any one of claims 1 or 2 with a pharmaceutically acceptable carrier, excipient or diluent.

6. A process for preparing a compound according to any one of claims 1 or 2 comprising reacting a non-sulphamated ring structure of formula D, E, F, G or H with a sulphamoylating agent to form the compound.

* * * * *